US007985537B2

(12) United States Patent
Zheng et al.

(10) Patent No.: US 7,985,537 B2
(45) Date of Patent: Jul. 26, 2011

(54) METHODS FOR DETERMINING THE HAIR FOLLICLE INDUCTIVE PROPERTIES OF A COMPOSITION

(75) Inventors: Ying Zheng, West Chester, PA (US); Satish Parimoo, Bridgewater, NJ (US); Kurt Stricker Stenn, Princeton, NJ (US)

(73) Assignee: Aderans Research Institute, Inc., Marietta, GA (US)

( * ) Notice: Subject to any disclaimer, the term of this patent is extended or adjusted under 35 U.S.C. 154(b) by 888 days.

(21) Appl. No.: 11/811,744

(22) Filed: Jun. 12, 2007

(65) Prior Publication Data

US 2008/0311044 A1 Dec. 18, 2008

(51) Int. Cl.
C12Q 1/00 (2006.01)
(52) U.S. Cl. .................. 435/4; 435/325; 435/371
(58) Field of Classification Search .................. None
See application file for complete search history.

(56) References Cited

U.S. PATENT DOCUMENTS

| | | | |
|---|---|---|---|
| 2,946,769 A | 7/1960 | Rose et al. | |
| 3,025,323 A | 3/1962 | Rose et al. | |
| 3,596,292 A | 8/1971 | Erb et al. | |
| 4,052,988 A | 10/1977 | Doddi et al. | |
| 4,104,195 A | 8/1978 | Ley et al. | |
| 4,209,607 A | 6/1980 | Shalaby et al. | |
| 4,226,243 A | 10/1980 | Shalaby et al. | |
| 4,343,931 A | 8/1982 | Barrows | |
| 4,384,061 A | 5/1983 | Reiter et al. | |
| 4,429,080 A | 1/1984 | Casey et al. | |
| 4,458,678 A | 7/1984 | Yannas et al. | |
| 4,505,266 A | 3/1985 | Yannas et al. | |
| 4,529,792 A | 7/1985 | Barrows | |
| 4,604,097 A | 8/1986 | Graves, Jr. et al. | |
| 4,643,734 A | 2/1987 | Lin | |
| 4,719,917 A | 1/1988 | Barrows et al. | |
| 4,851,521 A | 7/1989 | della Valle et al. | |
| 4,919,664 A | 4/1990 | Oliver et al. | |
| 4,947,840 A | 8/1990 | Yannas et al. | |
| 5,061,284 A | 10/1991 | Laghi | |
| 5,091,173 A | 2/1992 | Buultjens et al. | |
| 5,133,739 A | 7/1992 | Bezwada et al. | |
| 5,141,522 A | 8/1992 | Landi | |
| 5,147,400 A | 9/1992 | Kaplan et al. | |
| 5,194,473 A | 3/1993 | Shinoda et al. | |
| 5,198,507 A | 3/1993 | Kohn et al. | |
| 5,286,837 A | 2/1994 | Barrows et al. | |
| 5,376,542 A | 12/1994 | Schlegal | |
| 5,403,347 A | 4/1995 | Roby et al. | |
| 5,423,778 A | 6/1995 | Eriksson et al. | |
| 5,486,593 A | 1/1996 | Tang et al. | |
| 5,502,092 A | 3/1996 | Barrows et al. | |
| 5,514,378 A | 5/1996 | Mikos et al. | |
| 5,522,841 A | 6/1996 | Roby et al. | |
| 5,545,208 A | 8/1996 | Wolff et al. | |
| 5,556,783 A | 9/1996 | Lavker et al. | |
| 5,578,046 A | 11/1996 | Liu et al. | |
| 5,599,552 A | 2/1997 | Dunn et al. | |
| 5,611,811 A | 3/1997 | Goldberg | |
| 5,661,132 A | 8/1997 | Eriksson et al. | |
| 5,667,961 A | 9/1997 | Bernard et al. | |
| 5,674,286 A | 10/1997 | D'Alessio et al. | |
| 5,677,355 A | 10/1997 | Shalaby et al. | |
| 5,690,961 A | 11/1997 | Nguyen | |
| 5,697,901 A | 12/1997 | Eriksson | |
| 5,697,976 A | 12/1997 | Chesterfield et al. | |
| 5,712,169 A | 1/1998 | Bernard et al. | |
| 5,721,049 A | 2/1998 | Marcolongo et al. | |
| 5,723,508 A | 3/1998 | Healey et al. | |
| 5,756,094 A | 5/1998 | Lavker et al. | |
| 5,767,152 A | 6/1998 | Nielsen et al. | |
| 5,770,417 A | 6/1998 | Vacanti et al. | |
| 5,817,120 A | 10/1998 | Rassman | |
| 5,847,012 A | 12/1998 | Shalaby et al. | |
| 5,891,426 A | 4/1999 | Jarrousse et al. | |
| 5,898,040 A | 4/1999 | Shalaby et al. | |
| 5,919,893 A | 7/1999 | Roby et al. | |
| 5,939,323 A | 8/1999 | Valentini et al. | |
| 5,945,115 A | 8/1999 | Dunn et al. | |
| 5,968,546 A | 10/1999 | Baur et al. | |
| 5,989,279 A | 11/1999 | Rassman | |
| 5,993,374 A | 11/1999 | Kick | |
| 5,997,468 A | 12/1999 | Wolff et al. | |
| 5,997,568 A | 12/1999 | Liu | |
| 6,001,378 A | 12/1999 | Desjonqueres | |
| 6,027,744 A | 2/2000 | Vacanti et al. | |
| 6,031,148 A | 2/2000 | Hayes et al. | |
| 6,051,750 A | 4/2000 | Bell | |

(Continued)

FOREIGN PATENT DOCUMENTS

CA 2140090 8/1995

(Continued)

OTHER PUBLICATIONS

Tilney N. L. et al. The Biology of Acute Transplant Rejection, Annals of Surgery, Aug. 1991, vol. 214, No. 2, pp. 98-106.*
Pintar T. et al. Skin Biopsies Predict Acute Graft-Verses-Host Disease After Small Bowl Trnasplantation in Pigs, Acta Veterinaria Hungarica, 2007, vol. 55, No. 4, pp. 533-541.*
Arase, S. et al., "Co-culture of human hair follicles and dermal papillae in a collagen matrix," J. Dermatol. (1990) 17:667-676.
Arase, Seigi, et al., "Culture of dispersed hair follicle cells from plucked out hairs without a feeder layer," Tokushima J. exp. Med. (1989) 36:87-95.
Atala A. (2004) Tissue engineering and regenerative medicine: concepts for clinical application. Rejuvenation Res 7:15-31.

(Continued)

*Primary Examiner* — Jon P Weber
*Assistant Examiner* — Satyendra K Singh
(74) *Attorney, Agent, or Firm* — Pabst Patent Group LLP

(57) ABSTRACT

The present invention provides a method for determining hair inductive properties of a composition comprising injecting a composition comprising dissociated dermal cells and epidermal cells into skin of a mammal and determining whether at least one hair follicle forms.

10 Claims, 5 Drawing Sheets

U.S. PATENT DOCUMENTS

| | | | |
|---|---|---|---|
| 6,093,200 A | 7/2000 | Liu et al. |
| 6,120,788 A | 9/2000 | Barrows |
| 6,147,135 A | 11/2000 | Yuan et al. |
| 6,159,950 A | 12/2000 | Crystal et al. |
| 6,333,029 B1 | 12/2001 | Vyakarnam et al. |
| 6,350,284 B1 | 2/2002 | Tormala et al. |
| 6,365,172 B1 | 4/2002 | Barrows |
| 6,383,220 B1 | 5/2002 | van Blitterswijk et al. |
| 6,423,252 B1 | 7/2002 | Chun et al. |
| 6,474,344 B2 | 11/2002 | Yamada |
| 6,503,539 B2 | 1/2003 | Gestrelius et al. |
| 6,511,748 B1 | 1/2003 | Barrows |
| 6,548,058 B1 | 4/2003 | Hunziker et al. |
| 6,569,143 B2 | 5/2003 | Alchas et al. |
| 6,613,798 B1 | 9/2003 | Porter et al. |
| 6,639,051 B2 | 10/2003 | Wang |
| 6,673,603 B2 | 1/2004 | Baetge et al. |
| 6,699,287 B2 | 3/2004 | Son et al. |
| 6,730,513 B1 | 5/2004 | Hunziker et al. |
| 6,773,713 B2 | 8/2004 | Bonassar et al. |
| 6,878,383 B2 | 4/2005 | Boss, Jr. et al. |
| 6,884,427 B1 | 4/2005 | Barrows |
| 7,198,641 B2 | 4/2007 | Barrows |
| 2002/0049426 A1 | 4/2002 | Butler et al. |
| 2002/0090725 A1 | 7/2002 | Simpson et al. |
| 2002/0172705 A1 | 11/2002 | Murphy et al. |
| 2002/0193740 A1 | 12/2002 | Alachas et al. |
| 2002/0193778 A1 | 12/2002 | Alachas et al. |
| 2003/0009113 A1 | 1/2003 | Olson |
| 2003/0049839 A1 | 3/2003 | Romero-Ortega et al. |
| 2003/0072784 A1 | 4/2003 | Williams |
| 2003/0077311 A1 | 4/2003 | Vyakarnam et al. |
| 2003/0077823 A1 | 4/2003 | Li et al. |
| 2003/0134099 A1 | 7/2003 | Barrows |
| 2003/0147831 A1 | 8/2003 | Marko |
| 2003/0161815 A1 | 8/2003 | Wolowacz et al. |
| 2003/0166274 A1 | 9/2003 | Hewitt et al. |
| 2003/0195625 A1 | 10/2003 | Garcia Castro et al. |
| 2003/0198646 A1 | 10/2003 | Stenn |
| 2003/0203003 A1 | 10/2003 | Nelson et al. |
| 2003/0235813 A1 | 12/2003 | Luyten et al. |
| 2004/0033598 A1 | 2/2004 | Vacanti et al. |
| 2004/0039438 A1 | 2/2004 | Alt |
| 2004/0057937 A1 | 3/2004 | Jahoda et al. |
| 2004/0068284 A1 | 4/2004 | Barrows |
| 2004/0220589 A1 | 11/2004 | Feller |
| 2005/0089512 A1 | 4/2005 | Schlotmann et al. |
| 2005/0147652 A1 | 7/2005 | Atkins et al. |
| 2005/0191748 A1 | 9/2005 | Barrows |
| 2005/0214344 A1 | 9/2005 | Barrows |
| 2005/0233450 A1 | 10/2005 | Goetinck et al. |
| 2005/0272150 A1 | 12/2005 | Teumer et al. |
| 2006/0057126 A1 | 3/2006 | Tankovich |
| 2006/0062770 A1 | 3/2006 | Zheng et al. |
| 2007/0092496 A1 | 4/2007 | Zheng et al. |
| 2007/0122387 A1 | 5/2007 | Cochran et al. |
| 2007/0148138 A1 | 6/2007 | Barrows et al. |
| 2007/0233038 A1 | 10/2007 | Pruitt et al. |

FOREIGN PATENT DOCUMENTS

| | | |
|---|---|---|
| CA | 2199918 | 9/1997 |
| CN | 1594554 | 3/2005 |
| EP | 405656 | 1/1991 |
| EP | 0236014 | 7/1991 |
| EP | 1002859 | 5/2000 |
| EP | 971679 | 6/2002 |
| EP | 0845963 | 9/2003 |
| EP | 1083874 | 1/2004 |
| EP | 1089704 | 2/2004 |
| EP | 1098626 | 5/2004 |
| EP | 1437042 | 7/2004 |
| EP | 1612265 | 1/2006 |
| EP | 1702632 | 9/2006 |
| JP | 3273028 | 12/1991 |
| JP | 4108444 | 4/1992 |
| JP | 7048769 | 2/1995 |
| JP | 10136977 | 5/1998 |
| JP | 11180878 | 7/1999 |
| JP | 2000187030 | 7/2000 |
| JP | 2000229889 | 8/2000 |
| JP | 2001302520 | 10/2001 |
| JP | 2002145701 | 5/2002 |
| JP | 2003070466 | 3/2003 |
| JP | 2003189849 | 7/2003 |
| JP | 2003235990 | 8/2003 |
| JP | 2003238421 | 8/2003 |
| JP | 2003328229 | 11/2003 |
| WO | WO 98/44027 | 10/1998 |
| WO | WO 98/47471 | 10/1998 |
| WO | WO 99/01034 | 1/1999 |
| WO | WO 99/34750 | 7/1999 |
| WO | WO 99/62491 | 12/1999 |
| WO | WO 00/03749 | 1/2000 |
| WO | WO 00/29553 | 5/2000 |
| WO | WO 00/45736 | 10/2000 |
| WO | WO 00/62829 | 10/2000 |
| WO | WO 01/58413 | 8/2001 |
| WO | WO 01/66472 | 9/2001 |
| WO | WO 01/70132 | 9/2001 |
| WO | WO 01/70289 | 9/2001 |
| WO | WO 01/70290 | 9/2001 |
| WO | WO 01/70291 | 9/2001 |
| WO | WO 02/40645 | 5/2002 |
| WO | WO 02/060396 | 8/2002 |
| WO | WO 03/022043 | 3/2003 |
| WO | WO 03/055990 | 7/2003 |
| WO | WO 03/057152 | 7/2003 |
| WO | WO 03/068248 | 8/2003 |
| WO | WO 03/088935 | 10/2003 |
| WO | WO 03/104443 | 12/2003 |
| WO | WO 02/15952 | 4/2004 |
| WO | WO 2004/044188 | 5/2004 |
| WO | WO 2005/018731 | 3/2005 |
| WO | WO 2005/033302 | 4/2005 |
| WO | WO 2005/053763 | 6/2005 |
| WO | WO 2005/097221 | 10/2005 |
| WO | WO 2006/020958 | 2/2006 |
| WO | WO 2006/057542 | 6/2006 |
| WO | WO 2007/047707 | 4/2007 |
| WO | WO 2007/062386 | 5/2007 |
| WO | WO 2007/062387 | 5/2007 |
| WO | WO 2007/092929 | 8/2007 |

OTHER PUBLICATIONS

Atlas of Anatomy Barron's Educational Series, Inc., 1997, p. 72.

Auger et al., "A truly new approach for tissue engineering: the LOEX self-assembly technique" Ernst Schering Res. Found. Workshop (2002) 35:73-88.

Barrows TH, Cochran SA, Griffin EI and Solomon AR, "Tissue Engineered Human Hair: Preliminary Clinical Results" TE2002: International Workshop on Tissue Engineering, St. Gallen, Switzerland (Feb. 2002).

Bieberich et al., "Differential expresion of the Hox 3.1 gene in adult mouse skin" Ann NY Acad Sci (1991) 642:346-354.

Bioglass Technology, U.S. Biomaterials Corporation, http://www.usbiomat.com/bioglass.html (Dec. 28, 2000) 4 pages.

Blanpain, C. et al., "Self-renewal, multipotency, and the existence of two cell populations within an epithelial stem cell niche," Cell (2004) 118:635-648.

Borue, X. et al., "Bone marrow-derived cells contribute to epithelial engraftment during wound healing," Am. J. Pathol. (2004) 165:1767-1772.

Bucala, R. et al., "Circulating fibrocytes define a new leukocyte subpopulation that mediates tissue repair," Mol. Med. (1994) 1:71-81.

Castex-Rizzi et al., "Implication of VEGF,steroid hormones and neuropeptides in hair follicle cell responses," Ann. Dermatol. Venereol. (2002) 129(5):783-786.

Chang et al. (2004) "Sculpting skin appendages out of epidermal layers via temporarally and spatially regulated apoptotic events" J Invest Dermatol 122:1348-1355.

Chase, H.B. et al., "Changes in the skin in relation to the hair growth cycle" The Anatomical Record, The Wistar Institute of Anatomy and Biology, Philadelphia, PA (1953) 116:75-81.

Chiang et al., 1999, "Essential Role for Sonic hedgehog during Hair Folllicle Morphogenesis" Dev. Biol. 205:1-9.

Christian et al., "Microarray analysis of human, rat, and mouse dermal papilla and connective sheath cells reveals multiple factors with potential for hair follicle growth regulations" J. Invest. Derm. (2002) 119(1):292.

Claudinot et al., "Long-term renewal of hair follicles from clonogenic multipotent stem cells," PNAS (2005) 102:14677-14682.

Cohen J, The transplantation of individual rat and guinea-pig whisker papillae. J Embryol Exp Morphol. Mar. 1961;9:117-27.

Cotsarelis G, Sun TT, Lavker RM. (1990) "Label-retaining cells reside in the bulge area of pilosebaceous unit. Implications for follicular stem cells, hair cycle and skin carcinogenesis," Cell 61:1329-1337.

Cotsarelis, G. et al., "Towards a molecular understanding of hair loss and its treatment," Trends Mol. Med. (2001) 7:293-301.

Deleens, G., et al., A new generation of thermoplastic elastomers the polyether block amide (PEBA), SPIE 39th Ann. Tech. Conf., Boston, MA (May 4-7, 1981) 13 pages.

Dlugosz, (1999), "The Hedgehog and the hair follicle: a growing relationship", The Journal of Clinical Investigation, vol. 104, 851-853.

Domashenko, et al., (2000), "Efficient delivery of transgenes to human hair follicle progenitor cells using topical lipoplex", Nature Biotechnology, vol. 18, 420-423.

Dry, F.W., "The coat of the mouse (*Mus musculus*)," J. Genetics, Bateson and Punnett eds., (1926) 287-340.

Du Cros et al. (1995) Association of versican with dermal matricies and its potential role in hair follicle development and cycling: J Invest Dermatol 105:426-31.

Dyce et al., (2004) "Stem cells with multilineage potential derived from porcine skin" Bioche Biophys Res Commun, 316:651-658.

Ebling FJ, "The biology of hair" Dermatol Clin Jul. 1987;5(3):467-81.

Evans, G.R. et al., "In vivo evaluation of poly(L-lactic acid) porous conduits for peripheral nerve regeneration," Biomaterials (1999) 20:1109-1115.

Favier B, et al. "Localisation of members of the notch system and the differentiation of vibrissa hair follicles: receptors, ligands, and fring modulators" Dev Dyn Jul. 2000;218(3):426-37.

Ferraris et al., 1997,"Adult epidermal keratinocytes are endowed with pilosebaceous forming abilities" Int. J. Dev. Biol., 41:491-498.

Fieser, L.F. and Fieser, M., "Reagents for Organic Synthesis," John Wiley and Sons, Inc. (1967) 704-706.

Foitzek, K. et al., "Prolactin and its receptor are expressed in murine hair follicle epithelium, show hair cycle-dependent expression, and induce catagen," Am. J. Path. (2003) 162(5):1611-1621.

Foitzik, et al., (2000) "Control of murine hair follicle regression (catagen) by TGF-B1 in vitro", Catagen Induction by TGF-B1, The FASEB Journal, vol. 14, 752-760.

Fujie et al. (2001) "The chemotactic effect of a dermal papilla cell-derived factor on outer root sheath cells," J. Dermatol. Sci. 25(3):206-12.

Gharzi et al., "Plasticity of hair follicle dermal cells in wound healing and induction," Exp. Dermat. (2003) 12:126-136.

Gho et al., "Hair transplantation of plucked hair biopsies," Dermatol. Surg. (2001) 27(10):913.

Gho et al. To Multiply or Not to Multiply, That is the Question . . . , Dr. Coen Gho presentation at the International Society of Hair Restoration Surgeons 2003 New York City Conference, Oct. 19, 2003 (Abstract).

Hardy M, "The development of mouse hair in vitro wit some observations on pigmentation" J. Anat (1949) 83:364-384.

Hardy, M., "The secret life of the hair follicle," Trends in Genetics (1992) 8:55-61.

Hashimoto et al., "Histological examination of human hair follicles grafted onto severe combined immunodeficient (SCID) mice," Hair Research for the Next Millenium eds., DJJ Van Neste and VA Randall, Elsevier Science BV, Amsterdam (1996) 141-145.

Hoffmann et al., "Aromatase and oxidative 3alpha-hydroxysteroid dehydrogenase are present in human hair follicles and regulate intrafollicular DHT levels," J. Invest. Derm. (2002) 119(1):292 Abstract.

Hoffmann et al., "Steroid sulfatase in the human hair follicle concentrates in the dermal papillae," J. Invest. Dermatol. (2001) 117:1342-1348.

Hoffmann, "Hormonal interaction and hair growth," Ann. Dermatol. Venereol. (2002) 129(5):787-792.

Hoffmann, R. et al., "17alpha-estradiol induces aromatase activity in intact human anagen hair follicles ex vivo," Exp. Dermatol. (2002) 11:376-380.

Horch, R.E. et al., "Tissue engineering of cultured skin substitutes," J. Cell Mol. Med. (2005) 9(3):592-608.

Horne et al., "Restoration of hair growth by surgical implantation of follicular dermal sheath," Development (1992) 116(3):563-571 Abstract.

Horne, Kenneth A, et al. "Whisker growth induced by implantation of cultured vibrissa dermal papilla cells in the adult rat" J Embryol Exp Morphol. Sep. 1986;97:111-24.

Hu M, Sabelmann EE, Lai S, Timek EK, Zhang F, Hentz, VR and Lineaweaver, CW, Journal of Biomedical Materials Research, vol. 47, pp. 79-84 (1999).

Ibraheem, M. et al., "Growth and viability of secondary hair follicles of the Angora goat cultured in vitro," J. Anatomy (1993) 182(2):231-238.

Iguchi et al., "Human follicular papilla cells carry out nonadipose tissue production of leptin," J. Invest. Dermatol. (2001) 117:1349-1356.

Ihara, S. et al., "Formation of hair follicles from a single-cell suspension of embryonic rat skin by a two-step procedure in vitro," Cell Tissue Res. (1991) 266:65-73.

Inaba (1992) "Chapter 16. The Question of Hair Regeneration. In: Human Body Odor, Etiology Treatment and Related Factors" Springer-Verlag, Tokyo (printed in Hong Kong) 235-260.

Inamatsu et al., "Establishment of rat dermal papilla cell lines that sustain the potency to induce hair follicles from afollicular skin" J Invest Dermatol. Nov. 1998;111(5):767-75.

Inui et al., "Androgen-inducible TGF-beta1 from balding dermal papilla cells inhibits epethelial growth: a clue to understand paradoxical effects of androgen on human hair growth," FASEB J (2002) 16(14):1967-1969.

Jahoda and Oliver, "The growth of vibrissa dermal papilla cells in vitro," Br. J. Dermatol. (1981) 105:623-627.

Jahoda and Reynolds (2001) "Hair follicle dermal sheath cells: unsung participants in wound healing" Lancet 358:1445-1448.

Jahoda CA, "Induction of follicle formation and hair growth by vibrissa dermal papillae implanted into rat ear wounds: vibrissa-type fibres are specified" Development. Aug. 1992;115(4):1103-9.

Jahoda Cab, et al. (1993) "Induction of Hair Growth in Ear Wounds by Cultured Dermal Papilla Cells" J Invest Dermatol 101(4):584-590.

Jahoda Cab, et al., (1996) "Human Hair follicle regeneration following amputation and grafting into the nude mouse" J Invest Dermatol, 107(6):804-807.

Jahoda Cab, et al., "Induction of hair growth by implantation of cultured dermal papilla cells" Nature. Oct. 11-17, 1984;311(5986):560-2.

Jahoda et al. "Dermal-Epidermal Interactions, Adult Follicle-Derived Cell Populations and Hair Growth" Dermatologic Clinics W. B. Saunders Co. London G.B., Oct. 1996, 14(4):573-583; XP002913549.

Jahoda, C.A.B. et al., "Hair follicle dermal cells differentiate into adipogenic and osteogenic lineages," Exp. Dermatol. (2003) 12:849-859.

Jahoda, Cab, et al., "Dermal-epidermal interactions—follicle-derived cell populations in the study of hair-growth mechanisms," Journal of Investigative Dermatology (1993) 101(1):33S-38S.

Jahoda, et al., "Trans-species hair growth induction by human hair follicle dermal papillae," Exp. Dermatol. (2001) 10:229-237.

Jiang, Y. et al., "Pluripotency of mesenchymal stem cells derived from adult marrow," Nature (2002) 418:41-49.

Kamimura, et al., "Primary mouse keratinocyte cultures contain hair follicle progenitor cells with multiple differentiation potential," Journal of Investigative Dermatology (1997) 109(4):534-540.

Katayama, S. et al., "Synthesis of Alternating Polyamide Esters by Melt and Solution Polycondensations of N,N'-Di(6-hydroxycaproyl)

dimines and N-6-Hydroxycaproyl Aminoalcohol with Terephthalic and Adipic Dimethyl Esters and Dichlorides" J. of Applied Polymer Science (1976) 20:975-994.

Kim et al., "Interferon beta secreted from human hair dermal papilla cells inhibits the growth outer root sheath cells cultured in vitro," Biochem. Biophys. Res. Commun. (2002) 290:1133-1138.

Kishimoto et al., "Role of versican in anagen hair induction during hair cycle," J. Invest. Derma. (2002) 119(1):287.

Kishimoto et al., "Selective activation of the versican promoter by epithelial- mesenchymal interactions during hair follicle development" Proc Natl Acad Sci U S A. Jun. 22, 1999;96(13):7336-41.

Kishimoto, et al., "Wnt signaling maintains the hair-inducing activity of the dermal papilla" Genes Dev. May 15, 2000;14(10):1181-5.

Krugluger, W. et al., "Reorganization of hair follicles in human skin organ culture induced by cultured human follicle-derived cells," Exp. Dermatol. (2005) 14(8):580-585.

Kulessa, H. et al., "Inhibition of Bmp signaling affects growth and differentiation in the anagen hair follicle," EMBO J. (2000) 19(24):6664-6674.

Lako et al., (2002) Hair follicle dermal cells repopulate the mouse haematopoietic system: J. Cell Sci 115:3967-3974.

Lavker, RM, et al., Hair follicle stem cells: Their location, role in hair cycle, and involvement in skin tumor formation, Journal of Investigative Dermatology (1993) 101(1):16S-26S.

Layer, P.G. et al., "Of layers and spheres: the reaggregate approach in tissue engineering," Trends Neurosci. (2002) 25:131-134.

Lee, K.H., "Tissue-engineered human living skin substitutes: development and clinical application," Yonsei Med. J. (2000) 41(6):774-779.

Li, A.G. et al., "Roles of TGFbeta signaling in epidermal/appendage development," Cytokine & Growth Factor Reviews (2003) 14(2):99-111.

Lichti et al., "In vivo regulation of murine hair growth: insights from grafting defined cell populations onto nude mice" J Invest Dermatol. Jul. 1993;101(1 Suppl):124S-129S.

Lichti, AB, et al., "Hair follicle development and hair growth from defined cell populations granted onto nude mice," J Invest Dermat (1995) 104(5):43S-44S.

Lin et al., "Activation of the notch pathway in the hair cortex leads to aberrant differentiation of the adjacent hair-shaft layers," Development (2000) 127:2421-2432.

Lindner, G. et al., "Involvement of hepatocyte growth factor/scatter factor and met receptor signal hair follicle morphogenesis and cycling," FASEB Journal (2000) 14(2):319-332.

Luo et al., U.S. Statutory Invention Registration H1610, Published Nov. 5, 1996, Methods for Culturing Hair Follicle Epithelial Matrix Cells.

Luo Y., et al. "Modification of Natural Polymers: Hyaluronic Acid," Methods of Tissue Engineering, Chapter 45, A. Atala and RP Lanza. eds., Academic Press (2002) 539-553.

Lyle, S. et al., "The C8/144B monoclonal antibody recognizes cytokeratin 15 and defines the location of human hair follicle stem cells," J. Cell Sci (1998) 111:3179-3188.

Ma, Peter X., Ruiyun Zhang, "Synthetic nano-scale fibrous extracellular matrix" J. Biomed. Materials Res. 46(1):60-72 (Jul. 1999) Abstract.

Magerl, M. et al., "Simple and rapid method to isolate and culture follicular papillae from human hair follicles," Exp. Dermatol. (2002) 11:381-385.

Malkinson F and Keane JT, (1978) "Hair Matrix Cell Kinettics; A Selective Review" Int'l J Dermatol, 17(7):536-551.

Matsuzaki et al., "Localization and migration of follicular melanocyte precursors in mouse vibrissae during hair cycle," Zoological Science (2002) 19(12):1450.

Matsuzaki et al., "The upper dermal sheath has a potential to regenerate the hair in the rat follicular epidermis," Differentiation (1996) 60(5):287-297 Abstract.

Mayorov, V.I. et al., "B2 elements present in the human genome," Mamm. Genome (2000) 11:177-179.

McElwee et al., "Cultured Peribulbar Dermal Sheath Cells Can Induce Hair Follicle Development and Contribute to the Dermal Sheath and Dermal Papilla" 2003 J. Invest Dermatol 121:1267-1275.

Messenger AG, "The control of hair growth: an overview" J Invest Dermatol Jul. 1993;101(1 Suppl):4S-9S.

Messenger, "Hair Follicle Tissue Culture" Br. J. Dermatol. (1985) 113:639-640.

Messenger, "The culture of dermal papilla cells from human hair follicles," British Journal of Dermatology (1984) 110:685-689.

Michel et al., "Characterization of a new tissue-engineered human skin equivalent with hair," In Vitro Cell Dev Biol. Anim. (1999) 35(6):318-326.

Misago, N. et al., "Proliferation and differentiation of organoid hair follicle cells co-cultured with fat cells in collagen gel matrix culture," Br. J. Dermatol. (1998) 139(1):40-48.

Miyashita et al., "Characterization of hair follicles induced in implanted, cultured rat keratinocyte sheets," Exp. Dermatol. (2004) 13(8):491-498.

Moore et al., "Extracellular matrix molecules and follicle mophogenesis in ovine skin," Reprod. Fertil. Devl. (2001) 13(2-3):143-149.

Morris RJ, Liu Y, Marles L, Yang Z, Trempus C, Li S, Lin JS, Sawicki JA, & Cotsarelis G. (2004) Capturing and profiling adult hair follicle stem cells. Nature Biotechnology 22:1-7.

Nakamura, M. et al., "Control of pelage hair follicle development and cycling by complex interaction between follistatin and activin," FASEB J (2003) 17:497-499.

Nam, Y.S. and T.G. Park, "Porous biodegradeable polymerick scaffolds prepared by thermally induced phase separation" The Journal of Biomedical Materials Research, Oct. 1999, 47(1): 8-17.

Nixon et al., "Regulation of prolactin receptor expression in ovine skin in relation to circulatory prolactin and wool follicle growth status," J. Endocrinol. (2002) 172:605-614.

Nixon et al., 1996, "Transforming Growth factor-alpha Immunoreactivity During Induced Hair Follicle Growth Cycles in Sheep and Ferrets" J. Histochem. Cytochem, 44:377-387.

Oliver RF (1980) "Local interactions in mammalian hair growth" Mammalian Hair Growth, 199-210.

Oliver RF and Jahoda Cab, (1989) "The Dermal Papilla and Maintenance of Hair Growth" Dermal Papilla and Hair Growth Chapter 4, 51-67. Cambridge: Cambridge University Press.

Oliver RF, (1971) "The dermal papilla and the development of hair growth" J Soc Cosmet Chem 22:741-755.

Oliver RF, "Whisker growth after removal of the dermal papilla and lengths of follicle in the hooded rat" J Embryol Exp Morphol. Jun. 1966;15(3):331-47.

Oliver RF, "Histological studies of whisker regeneration in the hooded rat." J Embryol Exp Morphol. Oct. 1966;16(2):231-44.

Oliver RF, "The experimental induction of whisker growth in the hooded rat by implantation of dermal papillae" .J Embryol Exp Morphol. Aug. 1967;18(1):43-51.

Oliver RF, "The induction of hair follicle formation in the adult hooded rat by vibrissa dermal papillae" J Embryol Exp Morphol. Feb. 1970;23(1):219-36.

Oliver, R.F., "Ectopic regeneration of whiskers in the hooded rat from implanted lengths of vibrissa follicle wall," J. Embryol. Exp. Morphol. (1967) 17:27-34.

Osada et al., "Characterization of vibrissa germinative cells: transition of cell types," Exp. Dermatol. (2001) 10:430-437.

Oshima et al., (2001) "Morphogenesis and renewal of hair follicles from adult multipotent stem cells" Cell, 104:233-245.

Ota et al., "Fibroblast growth factor 5 inhibits hair growth by blocking dermal papilla cell activation," Biochem. Biophys. Res. Comm. (2002) 290(1):169-176.

Patrick, C.W., et al., eds., "Prospectus of Tissue Engineering," Frontiers in Tissue Engineering, Elsiver Science, Inc., New York, (1998) 3-11.

Paus et al., "A comprehensive guide for the recognition and classification of distinct stages of hair follicle morphogenesis" J Invest Dermatol (1999) 113:523-532.

Paus, R. et al., "Telogen skin contains an inhibitor of hair growth," Brit J Dermatol (1990) 122:777-784.

Philpott et al., 1994, "Effects of Insulin and Insulin-Like Growth Factors on Cultured Human Hair Folicles: IGF-I at Physiologic Concentrations Is an Important Regulator of Hair Follicle Growth In Vitro" J. Invest. Derm., 120:857-861.

Philpott, M. et al., "In vitro maintenance of isolated hair follicles: current status and future development," Ex. Dermatol. (1999) 8(4):317-319 Abstract.
Pisansarakit, P. et al., "Cultivation of mesenchymal cells derived from the skin and hair follicles of the sheep the involvement of peptide factors in growth regulation," Arch Dermatol Res. (1991) 183(5):321-327 Abstract.
Pispa, J. and Thesleff, I., "Mechanisms of ectodermal organogenesis," Dev Biol (2003) 262:195-205.
Pouliot et al., "Reconstructed human skin produced in vitro and grafted on athymic mice," Transplantation (2002) 73(11):1751-1757.
Price, V.H., "Treatment of Hair Loss," N Eng J Med (1999) 341:964-973.
Prouty, S.M. et al., "Fibroblast-dependent induction of a murine skin lesion similar to human nevus sebaceus of jadassohn," Lab. Invest (1997) 6(2):179-189.
Prouty, S.M. et al., "Fibroblast-dependent induction of a murine skin lesion with similarity to human common blue nevus" Am J Pathol. (1996) 148(6):1871-1885.
Raposio, E. et al., "Follicular bisection in hair transplantation surgery: an in vitro model," Plastic and Reconstructive Surgery (1998) 221-226.
Rassman, W.R. et al., "Rapid fire hair implanter carousel," Dermatologic Surgery (1998) 24:623-627.
Ratner, B.D. et al., "Biomaterials: where we have been and where we are going," Annu. Rev. Biomed. Eng. (2004) 6:41-75.
Reginelli et al. (1995) "Digit tip regeneration correlates with regions of Msx1 (Hox 7) expression in fetal and newborn mice" Development 121:1065-1076.
Remmler D, et al., "Use of injectable cultured human fibroblasts for percutaneous tissue implantation," Arch Otolaryngol Head Neck Surg (1989) 115:837-844.
Rendl, M. et al., "Molecular dissection of mesenchymal-epithelial interactions in the hair follicle," PLOS Biol. (2005) 3(11):1910-1924.
Reynolds AJ and Jahoda CAB, (1991a) "Inductive Properties of Hair Follicle Cells" Annals New York Academy of Sciences, 624:226-242.
Reynolds AJ and Jahoda, CA, "Hair fibre progenitor: developmental status and interactive potential" Dev Biol (1993) 4:241-250.
Reynolds AJ, et al. (1992) "Human Hair Follical Germinative Epidermal Cell Culture" J Invest Dermatol,101(4): 634-638.
Reynolds AJ, Jahoda, CA, "Hair follicle reconstructive in vitro" J. Dermatol Sci Jul. 1994;7 Suppl:S84-97.
Reynolds and Jahoda, "Cultured dermal papilla cells induce follicle formation and hair growth by transdifferentiation of an adult epidermis" Development (1992) 115:587-593.
Reynolds, A.J., et al., "Trans-gender induction of hair follicles," Nature (1999) 402:33-34.
Robinson, M. et al., "Hair cycle stage of the mouse vibrissa follicle determines subsequent fiber growth and follicle behavior in vitro," J. Invest. Dermatol. (1997) 108:495-500.
Rogers et al. "Cultivation of murine hair follicles as organoids in a collagen matrix" J Invest Dermatol. Oct. 1987;89(4):369-79.
Sato, et al., "Induction of the hair growth phase in postnatal mice by localized transient expression of sonic hedgehog", J. Clin. Invest. (1999) 104:855-864.
Sawaya et al., "Effects of finasteride on apoptosis and regulation of the human hair cycle," J. Cutan Med. Surg. (2002) 6(1):1-9.
Saywell, D.P. et al., "Cell proliferation during fibre growth initiation in ferret hair follicles," Proceedings of the New Zealand Society of Animal Production (1992) 52:299-302.
Schmidt-Ullrich, R. et al., "Molecular principles of hair follicle induction and morphogenesis," Bioessays (2005) 27:247-261.
Schwarz, M.A. et al., "Epithelial-mesenchymal interactions are linked to neovacsularization" Amer J Respir Cell Mol Biol (2004) 30:784-792.
Soma et al., "Involvement of transforming growth factor-beta2 in catagen induction during human hair cycle," J. Invest. Dermatol. (2002) 118:993-997.
Stenn and Paus, "Controls of Hair Follicle Cycling" Physiological Reviews (2001) 81(1):449-494.

Stenn et al., "Bioengineering the hair follicle: fringe benefits of stem cell technology," Curr. Opin. in Biotech. (2005) 16:1-5.
Stenn et al., "Re-epithelialization," Chapter 14 in: The Molecular and Cellular Biology of Wound Repair, Eds, RAF Clark, Plenum Press (1988) 321-335.
Stenn KS, "Induction of hair follicle growth" J. Invest Dermatol (1991) 96(5):80S.
Stenn, et al., "Hair follicle growth controls," Dermatol Clinics (1996) 14:543-558.
Stenn, K. et al., "Growth of the Hair Follicle: A Cycling and Regenerating Biological System," The Molecular Basis of Epithelial Appendage Morphogenesis, ed. C-M Chuong, Landes Publ. Austin TX (1998) 111-130.
Stenn, K.S. et al., "Bioengineering the hair follicle: fringe benefits of stem cell technology," Curr. Opin. Biotech. (2005) 16(5):493-497.
Sundberg et al. (2000) "Asebia-2J(Scd1(ab2J)): a new allele and a model for scarring alopecia" Amer J Path 156:2067-2075.
Takeda, A. et al., "Histodifferentiation of hair follicles in grafting of cell aggregates obtained by rotation culture of embryonic rat skin" Scand J. Plas Reconstr Hand Surg (1998) 32:359-364.
Takeda, A. et al., "Reconstitution of hair follicles by rotation culture," Hair Research for the Next Millennium, eds. Van Neste and Randall, Elsevier Science BV (1996) 191-193.
Taylor et al., "Involvement of follicular stem cells in forming not only the follicle but also the epidermis" Cell (2000) 102:451-461.
Thornton, M.J. et al., "Ability to culture dermal papilla cells from red deer (*Cervus elaphus*) hair follicle differing hormonal responses in vivo offers a new model for studying the control follicle biology," J. Experimental Zoology (1996) 275(6):452-458.
Tomihata K and Ikada Y, "Crosslinking of hyaluronic acid with water-soluble carbodiimide" J. Biomed. Mater. Res. (1997) 37:243-251.
Trempus et al. "Enrichment for living murine keratinocytes from the hair follicle bulge with the cell surface marker CD34" J Invest Dermatol (2003) 120:501-511.
Warren, R. et al., "Improved method for the isolation and cultivation of human scalp dermal papilla cells," J. Invest. Dermatology (1992) 98(5):693-699.
Watson SAJ, et al., (1994) "Sheep vibrissa dermal papillae induce hair follicle formation in heterotypic skin equivalents" Br J Dermatol, 131:827-835.
Weinberg, et al. Reconstruction of hair follicle development in vivo: determination of follicle formation, hair growth, and hair quality by dermal cells: Journal of Investigative Dermatology 100(3), Mar. 1993, 229-235.
Widelitz et al., "Molecular Histology in Skin Appendage Morphogenesis" Microsc. Res. Tech. (1997) 38:452-465.
Widelitz, R.B. and Chuong, C-M., "Early events in skin appendage formation: Induction of epithelial placodes and condensation of dermal mesenchyme," J Invest Dermatol Sympos Proc (1999) 4(3):302-306.
Williams, D. et al., "Isolation and culture of follicular papillae from murine vibrissae: an introductory approach," Br. J. Dermatol. (1994) 130:290-297.
Wilson C. et al., "Cells withing the bulge region of moust hair follicle transiently proliferate during early anagen: heterogeneity and funtional differences of various hair cycles" Differentiation (1994) 55(2):127-36.
Worst, P.K.M. et al., "Reformation of organized epidermal structure by transplantation of suspensions and cultures of epidermal and dermal cells," Cell Tiss. Res. (1982) 225(1):65-77.
Xing, L and Kobayashi, K., "Ability of Transplanted Cultured Epithelium to Respond to Dermal Papillae," Tissue Engineering (2001) 7:535-544.
Yagita, "CD95 ligand graft rejection" Nature (1996) 379:682-683.
Yang et al., "Cell sheet engineering: recreating tissue without biodegradable scaffolds," Biomaterials (2005) 26(33):6415-6422.

Yang, et al., "Upper-Human Hair Follicle Contains a Subpopulation of Keratinocytes with Superior In Vitro Proliferative Potential", In vitro Growth of Follicular Keratinocytes, The Journal of Investigative Dermatology, (1993) 101(5):652-659.

Yano et al., "Control of hair growth and follicle size by VEGF-mediated angiogenesis," J. Clin. Invest. (2001) 107(4):409-417.

Yano, K. et al., "Thrombospondin-1 plays a critical role in the induction of hair follicle involution vascular regression during the catagen phase," J. Invest. Dermatol. (2003) 120:14-19.

Yuspa SH, et al., "Regulation of hair follicle development: An in vitro model for hair follicle invasion of dermis and associated connective tissue remodeling," J Invest Derm (1993) 101(1):27S-32S.

Zheng, Y. et al., "Organogenesis from dissociated cells: generation of mature cycling hair follicles from skin-derived cells," J. Invest. Dermatol. (2005) 124:867-876.

* cited by examiner

FIG. 6A
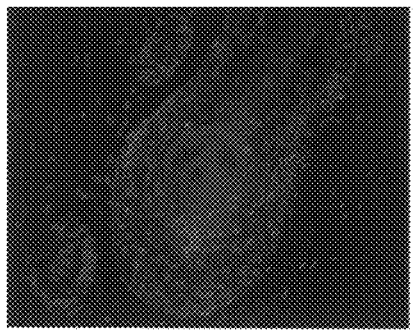
FIG. 6B
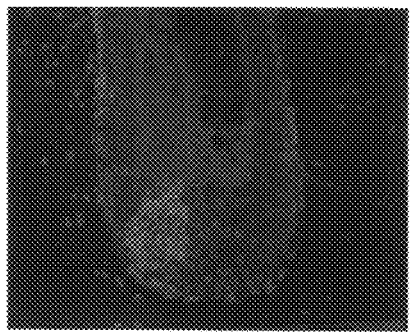
FIG. 6C
FIGS. 6A-6C

METHODS FOR DETERMINING THE HAIR FOLLICLE INDUCTIVE PROPERTIES OF A COMPOSITION

CROSS-REFERENCE TO RELATED APPLICATIONS

Not applicable

STATEMENT REGARDING FEDERALLY SPONSORED RESEARCH OR DEVELOPMENT

Not applicable

BACKGROUND

It has long been recognized that the hair follicle regenerates over the life time of an individual and reproduces its lower half cyclically. New follicle formation can be induced experimentally by cellular manipulation. Studies of the cells which contribute to new follicle formation have been limited by the ability to assay these same cells for their hair follicle inductive, or trichogenic, properties. Various assays have been developed to determine hair follicle inductive properties including hanging drop cultures, granulation tissue beds, collagenous shells, kidney capsule cultures and an assay using an immunoincompetent mouse and silicon chamber ("the Lichti/Prouty assay"). Notably, the Lichti/Prouty assay is demanding in terms of cell number, time and animals required. The assay allows for only one sample per mouse, requires large numbers of cells per graft, requires a surgically intensive procedure and requires four weeks for results. Accordingly, there is a need in the art for new methods for assessing the hair inductive properties of human and other mammalian cells.

SUMMARY

In one embodiment, the present invention provides a method for determining hair inductive properties of a composition comprising injecting a composition comprising dissociated dermal cells and epidermal cells into skin of a mammal, wherein the dermal cells are from a first species and epidermal cells are from a second species, and wherein the first species is different from the second species; and determining whether at least one hair follicle forms, wherein the hair follicle is associated with at least one sebaceous gland, and wherein formation of at least one hair follicle indicates that the composition has hair inductive properties.

In another embodiment, the present invention provides a method for determining hair inductive properties of a composition comprising injecting a composition comprising dissociated dermal cells and epidermal cells into skin of a mammal, wherein the dermal cells are from a first species and epidermal cells are from a second species, and wherein the first species is different from the second species; and determining whether at least one hair follicle forms, wherein the hair follicle comprises an outer root sheath, an inner root sheath with companion layer, and dermal papilla, and wherein formation of at least one hair follicle indicates that the composition has hair inductive properties.

In a further embodiment, the present invention provides a method for determining hair inductive properties of a composition comprising injecting a composition comprising dissociated dermal cells and epidermal cells into skin of a mammal, wherein the dermal cells and epidermal cells are from human; and determining whether at least one hair follicle forms, wherein the hair follicle is associated with at least one sebaceous gland, and wherein formation of at least one hair follicle indicates that the composition has hair inductive properties.

In yet another embodiment, the present invention provides a method for determining hair inductive properties of a composition comprising injecting a composition comprising dissociated dermal cells and epidermal cells into skin of a mammal, wherein the dermal cells and epidermal cells are human; and determining whether at least one hair follicle forms, wherein the hair follicle comprises an outer root sheath, an inner root sheath with companion layer, and dermal papilla, and wherein formation of at least one hair follicle indicates that the composition has hair inductive properties.

Other aspects of the invention will become apparent by consideration of the detailed description and accompanying drawings.

BRIEF DESCRIPTION OF THE DRAWINGS

FIGS. 6A-6C show newly formed hybrid hair follicles stained for human centromeres (green) and mouse centromeres (red).

DETAILED DESCRIPTION

Figure 1:
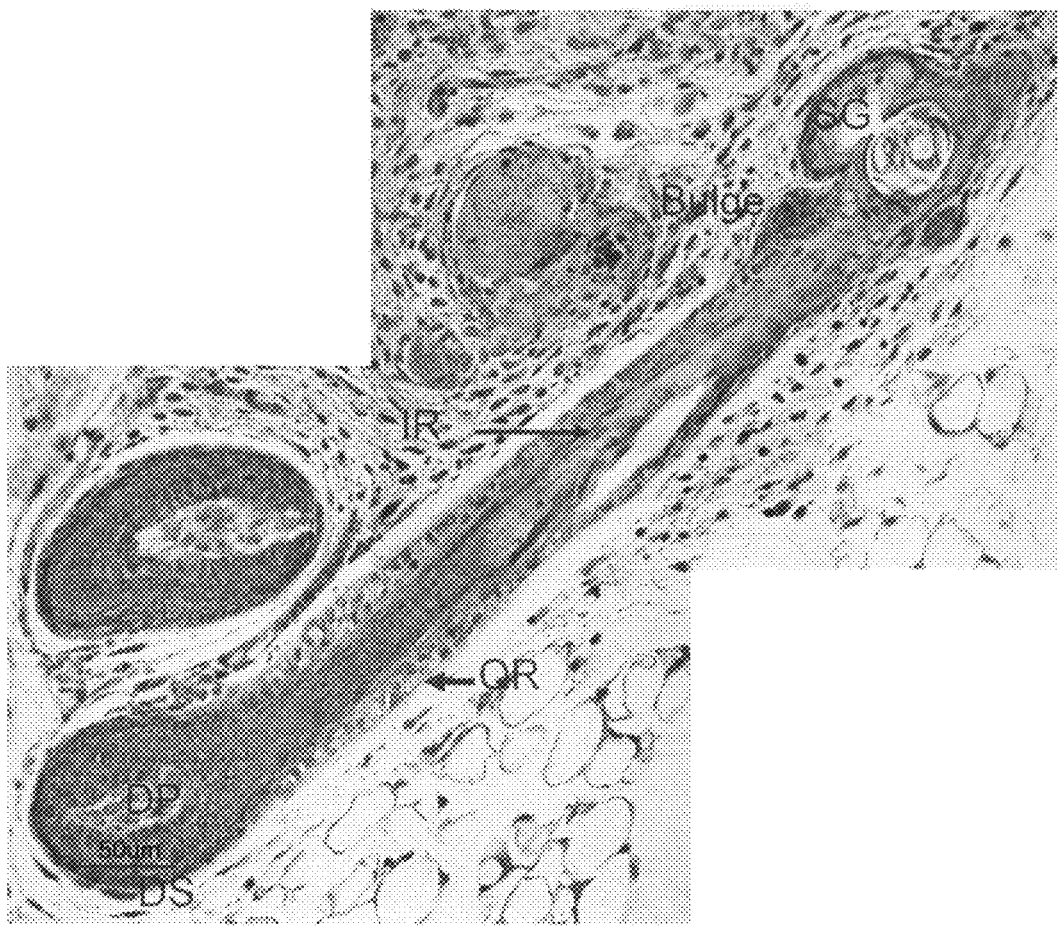
FIG. 1 shows the complete structure of a hair follicle formed from in example 1, including a sebaceous gland ("SG"), bulge, inner root sheath ("IR"), outer root sheath ("OR"), dermal papilla ("DP") and dermal sheath ("DS").
Figure 2:
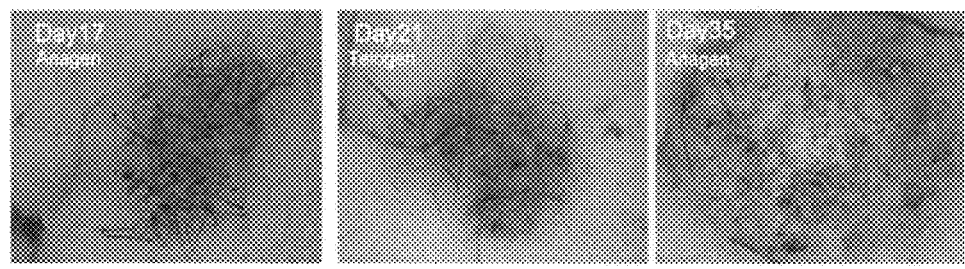
FIG. 2 demonstrates that the newly formed hybrid follicles of the invention going through normal hair cycles.

A novel method to determine the hair inductive properties of a composition comprising dissociated dermal and epidermal cells has been developed. The term "hair inductive properties" refers to the ability of cells to produce and/or induce new hair follicle formation. The term "trichogenic" may also be used to describe this property. The method comprises injecting a composition of cells into the skin of a mammal and determining whether at least one new hair follicle forms. A newly formed hair follicle may include the layered epithelial structure of a hair follicle, with a normal appearing hair shaft, internal root sheath with companion layer, dermal or follicular papilla and/or at least one sebaceous gland.

A newly formed hair follicle structure may have the ability to undergo cyclic growth demonstrating phases of anagen (the growing phase), catagen (the intermediate phase) and telogen (the shedding phase) similar to a naturally occurring hair follicle. A hair follicle formed during the method of the invention may cycle repeatedly through these phases or may only cycle a finite number of times or may only cycle once.

Suitably the dermal and epidermal cells are from different species to form a hybrid composition of cells. For example, the dermal cells may be from mouse and the epidermal cells may be from human. Alternatively, the dermal cells may be from human and the epidermal cells may be from mouse. The cells, whether dermal or epidermal, from mouse may be from a mouse of any age, e.g., a neonatal mouse or an adult mouse. Similarly, the cells from a human may be from a human of any age, including cells from neonatal foreskin. Cells from mouse and human are provided only as an example, other mammalian species may also be used in the methods of the invention. For example, dermal or epidermal cells may also be from rat or pig and combined with dermal or epidermal cells from mouse or human.

Alternatively, the composition of cells may be comprised of solely human cells, wherein the dermal and epidermal components are both from human. Though both components are from human, they need not be from the same human. Similarly, the dermal and epidermal components need not be from humans of the same or similar age. Accordingly, by way of example, the dermal cells may be from an adult human while the epidermal cells may be from neonatal foreskin.

Suitable cells are available commercially. For example, commercially available epidermal cells which may be used include, but are not limited to, adult or neonatoal, cryopreserved, human epidermal keratinocytes-APF from Cascade Biologics (Portland, Oreg.) or cryopreserved human outer root sheath cells from Cell Applications (San Diego, Calif.). Suitable commercially available culture media for epidermal cells includes, but is not limited to EPILIFE Medium from Cascade Biologics (Portland, Oreg.), defined keratinocyte serum-free medium ("DKSFM") from Invitrogen (Carlsbad, Calif.), BRFF-EPM 2—a complete serum-free medium from Athena Environmental Sciences (Baltimore, Md.), outer root sheath growth medium kit from Cell Applications (San Diego, Calif.) or keratinoctye serum-free growth medium from Cell Applications (San Diego, Calif.).

Similarly, commercially available dermal cells which may be used include, but are not limited to cryopreserved hair follicle dermal papilla cells from Cell Applications (San Diego, Calif.) and WI-38 VA-13 subline 2RA from Istituto Ricerche Farmacologiche Mario Negri (Milan, Italy), Suitable commercially available culture media for dermal cells includes, but is not limited to hair follicle dermal papilla growth media from Cell Applications (San Diego, Calif.), MEMα or Fetal Bovine Serum, Qualified and Heat-Inactivated, both from Invitrogen (Carlsbad, Calif.). Alternatively, the dermal and/or the epidermal cells may be isolated from a subject and cultured prior to inclusion in the assay composition.

The composition may be composed of about one million to about four million cells total. Suitably, the ratio of dermal cells to epidermal cells in the range of about 500:1 to about 1:100, more suitably in the range of about 100:1 to about 1:20 and most suitably about 20:1 to about 1:5. For example, a suitable composition which may be used in the methods of the invention may contain $1\times10^6$ human dermal cells with $5\times10^4$ mouse neonatal epidermal aggregates. Alternatively, another suitable composition may contain $0.5\times10^6$ human epidermal cells with 2 or $2.5\times10^6$ mouse neonatal dermal cells.

Suitably, the composition of epidermal and dermal cells may be combined with a pharmacologically suitable carrier such as saline solution, phosphate buffered saline solution, Dulbecco's Phosphate Buffered Saline ("DPBS"), DMEM, D-MEM-F-12 or HYPOTHERMOSOL-FRS from BioLifeSolutions (Bothell, Wash.) or a preservation solution such as a solution including, but not limited to, distilled water or deionized water, mixed with potassium lactobionate, potassium phosphate, raffinose, adenosine, allopurinol, pentastarch prostaglandin E1, nitroglycerin, and/or N-acetylcysteine into the solution. Suitably, the preservation solution employed may be similar to standard organ and biological tissue preservation aqueous cold storage solutions such as HYPOTHERMOSOL-FRS from BioLifeSolutions (Bothell, Wash.).

The composition and the carrier may be combined to form a suspension suitable for injection. Each injection may comprise about 20 μl to about 100 μl of composition or suspension. More suitably, the injection may comprise about 40 μl to about 90 μl of composition or suspension. Most suitably, the injection may comprise about 60 μl to about 80 μl of composition or suspension. The injection may be performed with any suitable needle, syringe or other instrument. Suitably, a 25 gauge needle attached to a syringe loaded with the composition or suspension may be used. Alternatively, a hubless insulin syringe may also be used to inject the composition into skin of a mammal. The suspension may also be delivered by other suitable methods, such as spreading the composition or suspension over superficial cuts of the skin or pipetting the composition or suspension into an artificially created wound.

The composition may be injected into skin of any suitable mammal. Most suitable is an immunocompromised mammal such as a nu/nu mouse, or nu/nu rat. The injection may be placed into any layer of the skin such as the deep dermis, the papillary dermis, the reticular dermis or the hypodermis. It is most suitable that the injected composition be placed in the skin such that the cells of the composition remain in a confined space, regardless of the particular layer, such that the cells are limited in the degree to which they may spread. For example, injection into the deep dermis is most suitable because the physical structure of the deep dermis limits the degree to which cells may spread upon injection.

In a further embodiment, the method of the present invention may be used to determine not only the hair inductive properties of the composition of cells alone, but may also be used in determining the effect of other components on the cells' hair inductive properties. Suitably, additional components include, but are not limited to growth factors such as fibroblast growth factors, placental growth factor or vascular endothelial growth factor, cytokines, proteins involved in organogenesis signaling such as sonic hedgehog homolog ("SHH"), a sonic hedgehog homolog agonist, proteins in the Wnt signaling pathway, noggin, or lymphoid enhancement factor ("LEF-1"), molecular constructs, cells altered ex vivo, pharmaceuticals, scaffold materials such as collagen, laminin, MATRIGEL or any other extracellular matrix proteins.

Alternatively, other components such as cellular scaffolds or scaffolding materials may be added to the composition. This method may also be used to test other properties of the hair such as pigmentation by adding various amounts of melanocytes from different donors into the cell combination As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical range recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification.

The following examples are provided to assist in a further understanding of the invention. The particular materials, methods and conditions employed are intended to be illustrative of the invention and are not limiting upon the scope of the invention.

EXAMPLE 1

Composition Injection into nu/nu mouse

Mature 6-14 week old *nu/nu* mice (Charles River Laboratories, Wilmington, Mass.) were anesthetized following USP IACUC approved protocol with ketamine (100 mg/kg) (Fort Dodge Animal Health, Iowa) or xylazine (10 mg/kg) (Phoenix Scientific Inc., St. Joseph, Mo.). A sedated animal was placed on a paper blanket in a tissue culture hood. The truncal surface of the animal was cleansed with 70% ethanol. Cellular compositions containing 1) dermal cells derived from C57/Black neonatal mouse (1-2 days old) (pregnant C57/Black female were purchased from Charles River Laboratories, Wilmington, Mass.) and neonatal human keratinocytes (Animal Product Free, Cascade Biologics, City State) cultured in EpiLife (Cascade Biologics, Portland, Oreg.) or BRFF-EPM2 (Athena Environmental Sciences Baltimore, Md.) or 2) hair follicle dermal papilla cells (Cell Applications, San Diego, Calif.) cultured in medium from Cell Applications (San Diego, Calif.) or WI-38 VA-13 subline 2RA cells from Istituto Ricerche Farmacologiche Mario Negri (Milan, Italy) cultured in MEMα (Invitrogen, Carlsbad, Calif.) with serum and epidermal cells derived from C57/Black neonatal mouse were suspended in DMEM/F-12. In this example, $1 \times 10^6$ human dermal cells were injected with $5 \times 10^4$ mouse neonatal epidermal aggregates or $0.5 \times 10^6$ human epidermal cells were injected with 2 or $2.5 \times 10^6$ mouse neonatal dermal cells. The cellular compositions were mixed with 60-80 ul DMEM/F-12 (Invitrogen, Carlsbad, Calif.). 60-80 μl of suspension was loaded into a syringe (Becton Dickinson, Franklin Lakes, N.J.) with a 25 gauge needle (Kendall Polypropylene Hub Hypodermic Needles, Mansfield, Mass., Catalog number 250313). An air bubble was allowed to form behind the sample and the base of the plunger to avoid introducing air bubbles into the cellular composition.

The cellular suspension was then slowly injected, up to 8-9 injections per mouse, into the deep dermis. The air bubble was also injected. The needle tip did not penetrate the whole dermis so that the cells of the composition can remain in a confined space in the dermis. Up to 8 injections were placed in each mouse. Each animal was tattooed at the site of implantation by piercing the skin peripheral to the injection site with a 25 gauge needle dipped in tattoo ink (242 Permanent Black Pigment, Aims, Hornell, N.Y.). Correspondingly, the left ear, right ear, both ears or the tail of the mouse was also tattooed or punched to distinguish individual mice in the same cage. The cage was then marked with the location of samples injected into each mouse, the experiment number and the date.

The injected cells were allowed to develop for 2-4 weeks. The cellular compositions comprised of mouse dermal cells and human epidermal cells required 14-20 days to form new hair follicles. The cellular compositions comprised of human dermal cells and mouse epidermal cells required 18-24 days to form hair follicles.

EXAMPLE 2

Injection Evaluation and Associated Histology

At the end of the incubation period the mice were sacrificed by $CO_2$ narcosis. The full-thickness skin was collected using dissecting forceps, scissors and a scalpel with scalpel blade. The tattooed spots on each mouse were used to ensure harvest of all the implantations. Also included in dissection were both ears (and/or the tail) for orientation and to distinguish individual mice from the same experiment.

The full-thickness skin was laid flat on a piece of paper towel moisturized with DPBS (Invitrogen, Carlsbad, Calif.) with the mucosal side in contact with the paper towel. The skin and paper towel were placed in a 10 cm dish. The cover of the dish was then secured with tape. Each dish was labeled with the location of the samples injected in each mouse, the experiment number and the date. The dish containing the full thickness skin was transported on ice.

In the same dish the full-thickness skin was fixed in 10% formalin or 4% freshly made paraformaldehyde in DPBS for two hours at room temperature. The fixed skin was then rinsed three times with DPBS for 10 minutes each time.

Using a dissecting microscope, the mucosal side of the full-thickness skin was examined for hair follicles. A small pigmented "bump" was sometimes observed. The "bump" was formed by epithelial cysts and soft tissue at each implantation site. If necessary, the "bump" was torn apart to see the hair follicles hidden inside. Alternatively, the "bump" was turned to the reverse side to see the hair follicle formed at the bottom of the bump. Some follicles were twisted, curled or malformed due to lack of space for the shaft outgrowth. Some observed follicles were very fine with light pigment and other follicles were partially formed with the bulb but not mature shafts. All of these various forms of hair follicles were included in the count of hair follicles. The dissociated dermal and epidermal cells were found to form the complete structure of the pilosebaceous unit including at least one sebaceous gland, a bulge, outer root sheath, inner root sheath, dermal papilla and a hair shaft. Usually about 1 to 20 follicles were found assay using human dermal and mouse neonatal epidermal cells. Usually 1 to 150 follicles were found per hybrid patch assay using human epidermal and mouse neonatal dermal cells.

EXAMPLE 3

Distinguishing Human and Mouse Cells in Newly Formed Follicles

Figure 3:
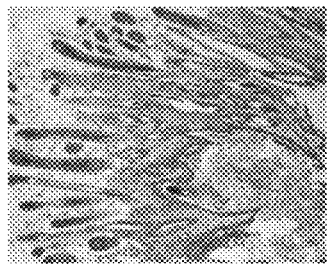
FIG. 3 shows the histology of the hair growth cycle.
Figure 3:
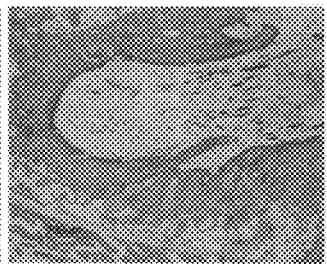
Figure 3:
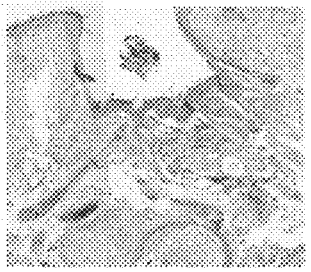
Figure 4:
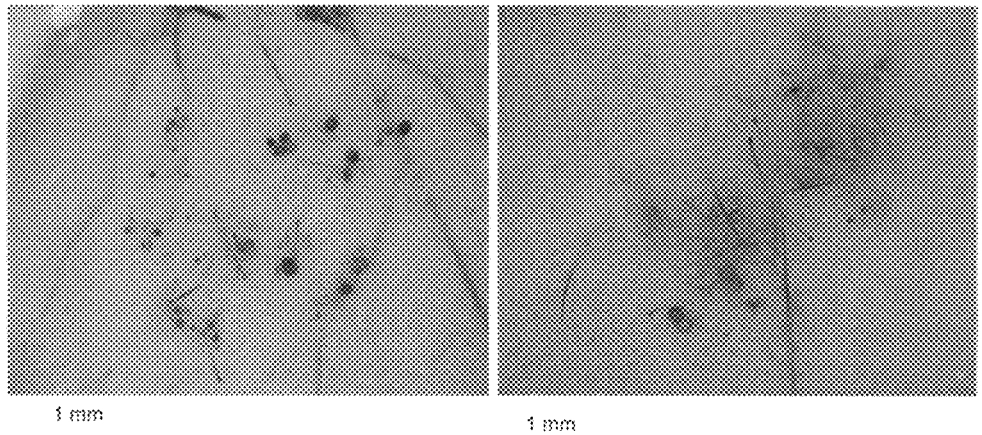
FIG. 4 shows new hair growth using the method of the invention using a composition of human dermal ($1 \times 10^6$) and mouse neonatal epidermal cells ($5 \times 10^4$ aggregates).
Figure 5:
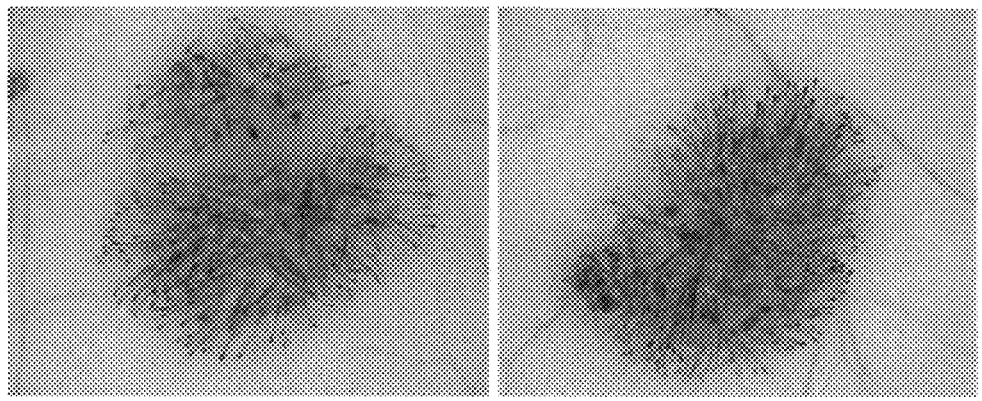
FIG. 5 shows new hair growth using method of the invention using a composition of human epidermal ($0.5 \times 10^6$) and mouse neonatal dermal cells ($2 \times 10^6$).

Staining with human or mouse-specific pan-centromere probes showed dynamic interaction between human and mouse cells. The human and mouse-specific pan-centromere probes were purchased from ID Labs Inc (human probe: CB1 579; mouse probe: CB1978M, 100 Collip Circle, Unit 117, London, ON Canada) As shown in FIGS. 3 and 4, the green represents human cells and the red represents mouse cells.

EXAMPLE 4

Study of Human Hair Follicle Cells in *nu/nu* Mice

The purpose of this experiment was to assess the ability of human hair follicle cells to grow in the immunocompromised mouse model. The starting materials for cell isolation were skin fragments or small pieces of scalp skin containing hair follicles from the Bosley hair transplant clinic in Philadelphia, Pa. The donors were males in their early 20s to late 60s. The tissues were rinsed in DPBS with antibiotics (1× penicillin/streptomycin/amphotericin ("PSA") (Invitrogen, Carlsbad, Calif.) and weighed. The tissue was placed in plastic centrifuge tubes, containing D-MEM/F-12 plus 1× PSA immediately after surgery. One hundred and fifty (150) cellular composition mixtures of $1 \times 10^6$ human dermal cells with 0.5 to $4.0 \times 10^6$ human epidermal cells were prepared. The injections were performed as in Example 1. The number of hair follicles were counted whenever applicable and recorded as in Example 1.

One of the 150 composition mixtures using human cells produced a new hair follicle in the nu/nu mouse. Usually only follicular structures were seen on histology, but in one case with freshly isolated dermal and epidermal cells, 4 defined hair follicles with hair shafts were observed. The follicles were identified by histology as human-mouse hybrids.

Various features and advantages of the invention are set forth in the following

What is claimed is:

1. A method for determining hair inductive properties of a composition comprising:
    injecting a composition comprising dissociated dermal cells and epidermal cells into the deep dermis of an immunocompromised mouse, wherein the dermal cells are from a first species and epidermal cells are from a second species and wherein the first species is different from the second species; and
    determining whether at least one hair follicle forms, wherein the hair follicle comprises an outer root sheath, an inner root sheath with companion layer, and dermal papilla; and wherein formation of at least one hair follicle indicates that the composition has hair inductive properties.

2. The method of claim 1, wherein the first species is mouse and the second species is human.

3. The method of claim 1, wherein the first species is human and the second species is mouse.

4. The method of claim 1, wherein from about one million to about five million cells are injected.

5. The method of claim 1, wherein the composition further comprises a carrier.

6. The method of claim 1, wherein the composition further comprises a component selected from the group consisting of growth factors, cytokines, proteins involved in organogenesis signaling, molecular constructs, cells altered ex vivo, pharmaceuticals, scaffold materials and combinations thereof.

7. A method for determining hair inductive properties of a composition comprising:
    injecting a composition comprising dissociated dermal cells and epidermal cells into the deep dermis of an immunocompromised mouse, wherein the dermal cells and epidermal cells are human; and
    determining whether at least one hair follicle forms, wherein the hair follicle comprises an outer root sheath, an inner root sheath with companion layer, and dermal papilla; and wherein formation of at least one hair follicle indicates that the composition has hair inductive properties.

8. The method of claim 7, wherein from about one to about five million cells are injected.

9. The method of claim 7, wherein the composition further comprises a carrier.

10. The method of claim 7, wherein the composition further comprises a component selected from the group consisting of growth factors, cytokines, proteins involved in organogenesis signaling, molecular constructs, cells altered ex vivo, pharmaceuticals, scaffold materials and combinations thereof.

* * * * *